United States Patent
Wang

(10) Patent No.: US 8,322,189 B2
(45) Date of Patent: *Dec. 4, 2012

(54) COMPREHENSIVE TWO-DIMENSIONAL GAS CHROMATOGRAPHY METHOD WITH ONE SWITCHING VALVE AS THE MODULATOR

(75) Inventor: Frank C. Wang, Annandale, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 325 days.

This patent is subject to a terminal disclaimer.

(21) Appl. No.: 12/583,167

(22) Filed: Aug. 14, 2009

(65) Prior Publication Data

US 2010/0050741 A1  Mar. 4, 2010

Related U.S. Application Data

(60) Provisional application No. 61/190,482, filed on Aug. 29, 2008.

(51) Int. Cl.
*G01N 7/00* (2006.01)
(52) U.S. Cl. ............... 73/23.22; 73/23.35; 73/23.37; 73/23.39; 73/23.4; 73/23.42; 95/82; 96/101
(58) Field of Classification Search ............... 73/23.42, 73/23.35, 23.22, 23.1, 23.37, 23.39, 23.4; 210/656; 95/82; 96/101
See application file for complete search history.

(56) References Cited

U.S. PATENT DOCUMENTS

| | | | | |
|---|---|---|---|---|
| 3,800,593 | A * | 4/1974 | Bradley | 73/864.81 |
| 4,534,207 | A * | 8/1985 | Szakasits et al. | 73/23.38 |
| 5,492,555 | A * | 2/1996 | Strunk et al. | 95/86 |
| 6,341,520 | B1 * | 1/2002 | Satoh et al. | 73/23.35 |
| 6,855,258 | B2 * | 2/2005 | Petro et al. | 506/12 |
| 7,096,886 | B2 | 8/2006 | Hofmann | |
| 7,779,670 | B2 * | 8/2010 | Wang | 73/23.42 |
| 2001/0037674 | A1 | 11/2001 | Petro et al. | |
| 2002/0020670 | A1 | 2/2002 | Petro | |
| 2004/0094482 | A1 | 5/2004 | Egorov et al. | |
| 2007/0214866 | A1 | 9/2007 | Wang | |

OTHER PUBLICATIONS

Wang, New Valve Switching Modulator For Comprehensive Two-Dimensional Gas Chromotography, Journal of Chromatography, Elsevier Science Publishers, vol. 1188, No. 2, pp. 274-280, Apr. 25, 2008.
Dugo et al, Comprehensive Multidimensional Liquid Chromotography: Theory and Applications, Journal of Chromatography, Elsevier Science Publishers, vol. 1184, No. 1-2, pp. 353-368, Feb. 28, 2008.
Tranchida et al, Comprehensive Chromatographic Methods for the Analysis of Lipids, Trends in Analytical Chemistry, Elsevier, vol. 26, No. 3, pp. 191-205, Mar. 2, 2007.
Supplementary European Search Report, EP09810376.

* cited by examiner

*Primary Examiner* — John Fitzgerald
*Assistant Examiner* — Hoang Nguyen
(74) *Attorney, Agent, or Firm* — Ronald D. Hantman; Glenn T. Barrett

(57) ABSTRACT

The present invention is an improvement to two-dimensional comprehensive gas chromatography. The improvement is a one valve switching modulator connecting the two separation columns. The valve includes either a two position eight-port valve or a two position twelve-port valve, and two transfer lines.

7 Claims, 5 Drawing Sheets

US 8,322,189 B2

COMPREHENSIVE TWO-DIMENSIONAL GAS CHROMATOGRAPHY METHOD WITH ONE SWITCHING VALVE AS THE MODULATOR

This application claims the benefit of U.S. Provisional Application 61/190,482 filed Aug. 29, 2008 and U.S. Ser. No. 11/716,325, filed Mar. 9, 2007 now U.S. Pat. No. 7,779,670.

BACKGROUND OF THE INVENTION

The present invention relates to a comprehensive two-dimensional gas chromatography system. In particular, the present invention relates to the modulator for such a system.

Comprehensive two-dimensional gas chromatography (GC×GC) is a powerful separation technique that provides the superior chromatographic type separation to a complex mixture. It is the most significant development in the gas chromatography technology area during recent years. The key to make a conventional GC into a comprehensive two-dimensional gas chromatography (GC×GC) is the modulation system. In the prior art, modulation is achieved by the trap and release mechanism called "thermal modulation". This method of modulation for GC×GC requires coolants (liquid nitrogen or liquid carbon dioxide) to operate. It is relatively inconvenient and it creates difficulty in the coolant handling situation, especially in the remote location or in the manufacture plant environment.

SUMMARY OF THE INVENTION

The present invention is an improvement to a comprehensive two-dimensional gas chromatography system. This improvement is a valve switching modulation system that has been designed and built for a comprehensive two-dimensional gas chromatography (GC×GC). In one embodiment, this valve switching modulation system utilizes one eight-port two-position switching valve to achieve the modulation. The valve system includes two transfer lines. In another embodiment, the valve switching modulation system utilizes one twelve-port two-position switching valve.

The advantages of using valve modulation for comprehensive two-dimensional gas chromatography are: (1) easy to understand and operate; (2) no extra external resource required; (3) unit design with either one eight-port two-position switching valve or one twelve-port two-position switching valve is especially attractive because of the simplicity. However, it is relatively difficult to design the experimental conditions to achieve the comprehensive two-dimensional analytical separation.

DETAILED DESCRIPTION OF THE PREFERRED EMBODIMENTS

Comprehensive two-dimensional gas chromatography is a recent development in the gas chromatography technical area. This new technique provides higher resolution, better sensitivity, and larger peak capacity. However, this new technique requires a modulation unit to manage this two dimensional separation. Most modulation unit design utilizes thermal modulation based on the pulsed trap-release mechanism with cold-hot gas flow throw through the modulation unit. This type of modulation unit requires a coolant, such as liquid carbon dioxide or liquid nitrogen, to perform the trap function.

A. One Eight-Port Two-Position Switching Valve

Figure 1:
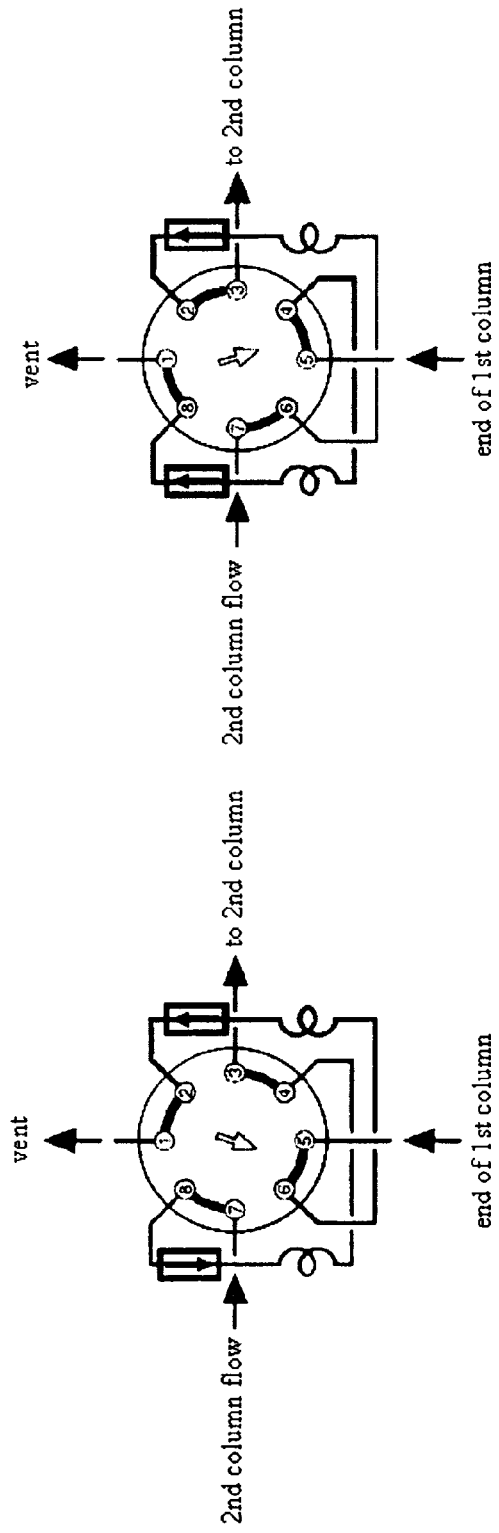
FIG. 1 shows a schematic diagram of one embodiment of the valve modulation system of the present invention.

The present invention uses a type of modulation unit design different from the thermal modulation, referred to as differential flow modulation, which is based on a switching valve and the secondary carrier gas flow to achieve the modulations function for comprehensive two-dimensional gas chromatography. The present invention is one eight-port two-position switching valve. FIG. 1 shows the design of the switching valve.

Figure 2:
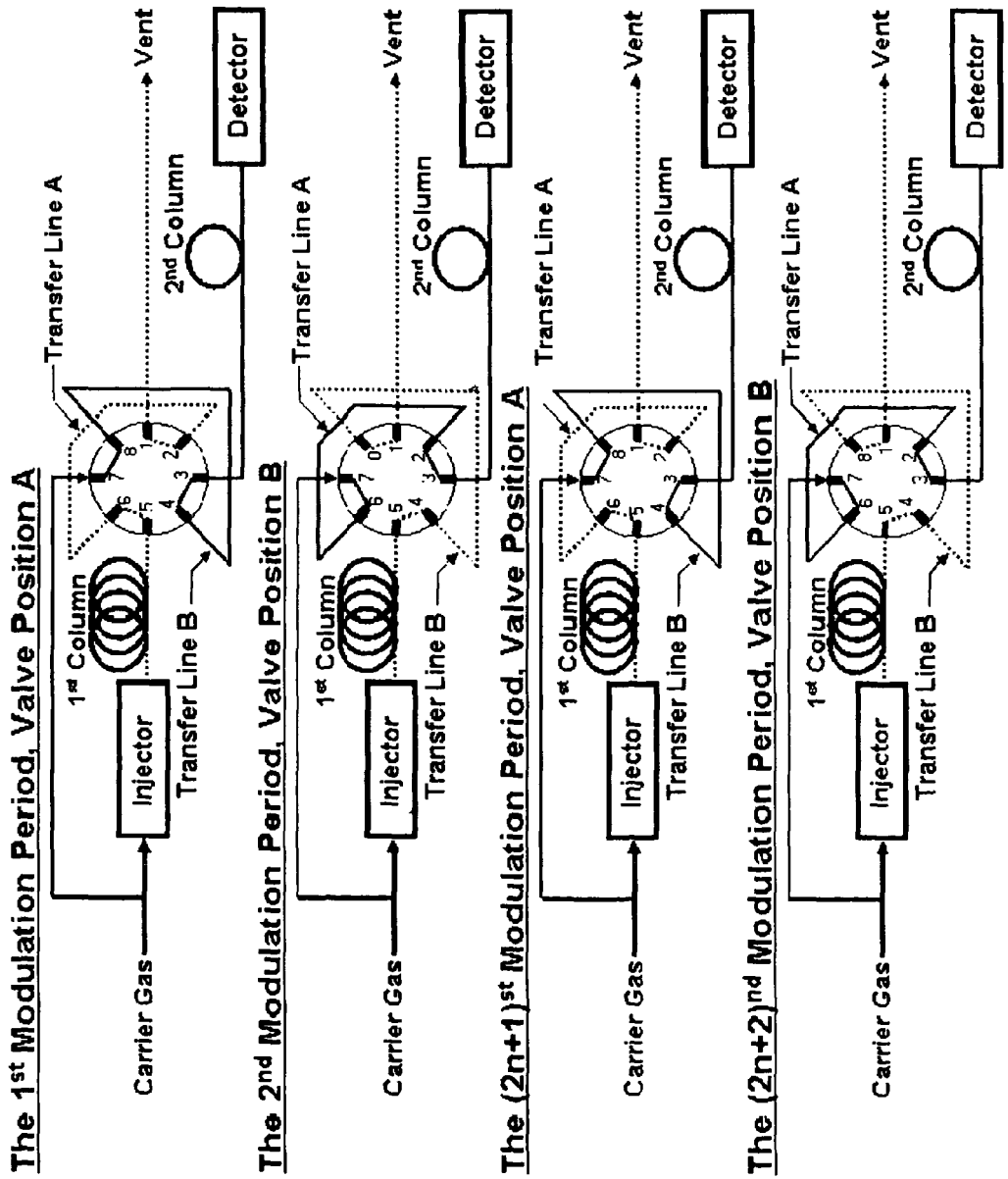
FIG. 2 shows a schematic diagram showing the flow of the fluid from the first column through the valve modulation system into the second column.

FIG. 2 shows a diagram of the switching valve showing the flow of fluid from the first column through the valve modulation system to the second column. When the valve is in position A at the $1^{st}$ or 2n+1 modulation period, the first column eluent is deposited in transfer line A and the eluent in transfer line B from the last modulation period is swept by the secondary carrier gas flow into the second column. In the next modulation period, the $2^{nd}$ or 2n+2 period, the valve switches to position B. The first column eluent then deposited in transfer line B and the eluent in transfer line A from the last modulation period is swept by the secondary carrier gas flow into the second column. By repeating this valve switching process, the modulation function is achieved and the comprehensive two-dimensional separation can be accomplished.

This invention describes a method to perform a comprehensive two-dimensional gas chromatography separation based on one eight-port two-position switching valve as a modulation unit. The separation is demonstrated with two examples; one for gasoline range hydrocarbon stream separation and the other one for the diesel temperature range hydrocarbon stream separation.

Experimental Set-Up and Conditions

The GC×GC system consists of an Agilent 6890 gas chromatograph (Agilent Technology, Wilmington, Del.) configured with inlet, columns, and detectors. A split/splitness inlet system with a 100-tray autosampler is used. The two-dimensional capillary column system utilizes a weak-polar first column (BPX-5, 30 meter, 0.25 mm I.D., 1.0 µm film), (SGE Inc. Austin, Tex., USA) and a polar (Sol-Gel Wax, 3 meter, 0.53 mm I.D., 1.0 µm film), (SGE Inc. Austin, Tex., USA) second column. A two-position, eight ports, switching valves modulation assembly based on FIG. 1 is installed between these two columns. The valve is electrical actuatored (VICI Valco Instruments Co. Inc., Houston, Tex., USA). The transfer line is a set of pre-cut ¹⁄₁₆ inch stainless steel tubing with 0.25 mmID and 30 cm length (Upchurch Scientific Inc. Oak Harbor, Wash., USA). The detector is a Flame ionization detector (FID) which comes with Agilent GC system.

Figure 3:
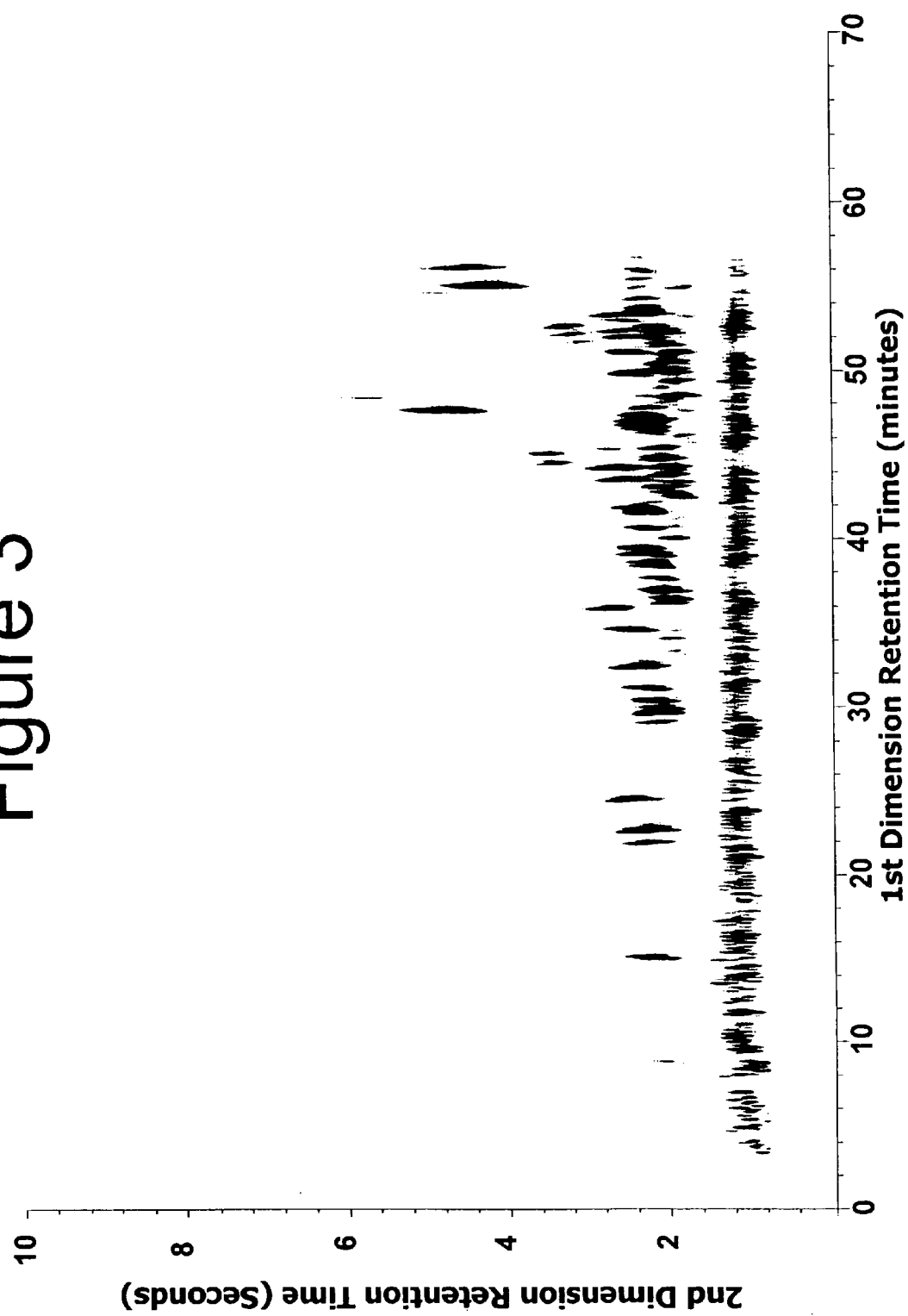
FIG. 3 shows a comprehensive two-dimensional gas chromatogram of heavy catalytic naphtha using the valve modulation system of the present invention.

After data acquisition, it was processed for qualitative analysis. The qualitative analysis converts data to a two-dimensional image that is processed by a commercial program "Transform" (Research Systems Inc. Boulder, Colo.). The two-dimensional image is further treated by "Photo-Shop" program (Adobe System Inc. San Jose, Calif.) to generate publication-ready images. FIG. 3 is the comprehensive two-dimensional gas chromatogram of the naphtha.

EXAMPLE 1

The Heavy Catalytic Naphtha Stream

The heavy catalytic naphtha stream used in this study is typical refinery streams boiling between 65° C. (150° F.) to 215° C. (420° F.) with carbon number from approximately $C_5$ to $C_{16}$.

A 0.2 μL sample was injected with 50:1 split at 300° C. in constant column flow mode at 1.5 mL per minute. The oven is programmed from 36° C. with 2 minute hold and 3° C. per minute increment to 180° C. with 0 minute hold and with total run time 50 minutes. The secondary carrier gas is in constant flow at 100 mL per minute. The modulation period is 8 seconds. The sampling rate for the detector was 100 Hz. FIG. 3 is the GC×GC chromatogram of the heavy catalytic naphtha stream.

EXAMPLE 2

The Diesel Stream

The diesel fuels used in this study are typical refinery streams boiling between 150° C. (300° F.) to 430° C. (800° C.) with carbon number from approximately $C_9$ to $C_{28}$.

Figure 4:
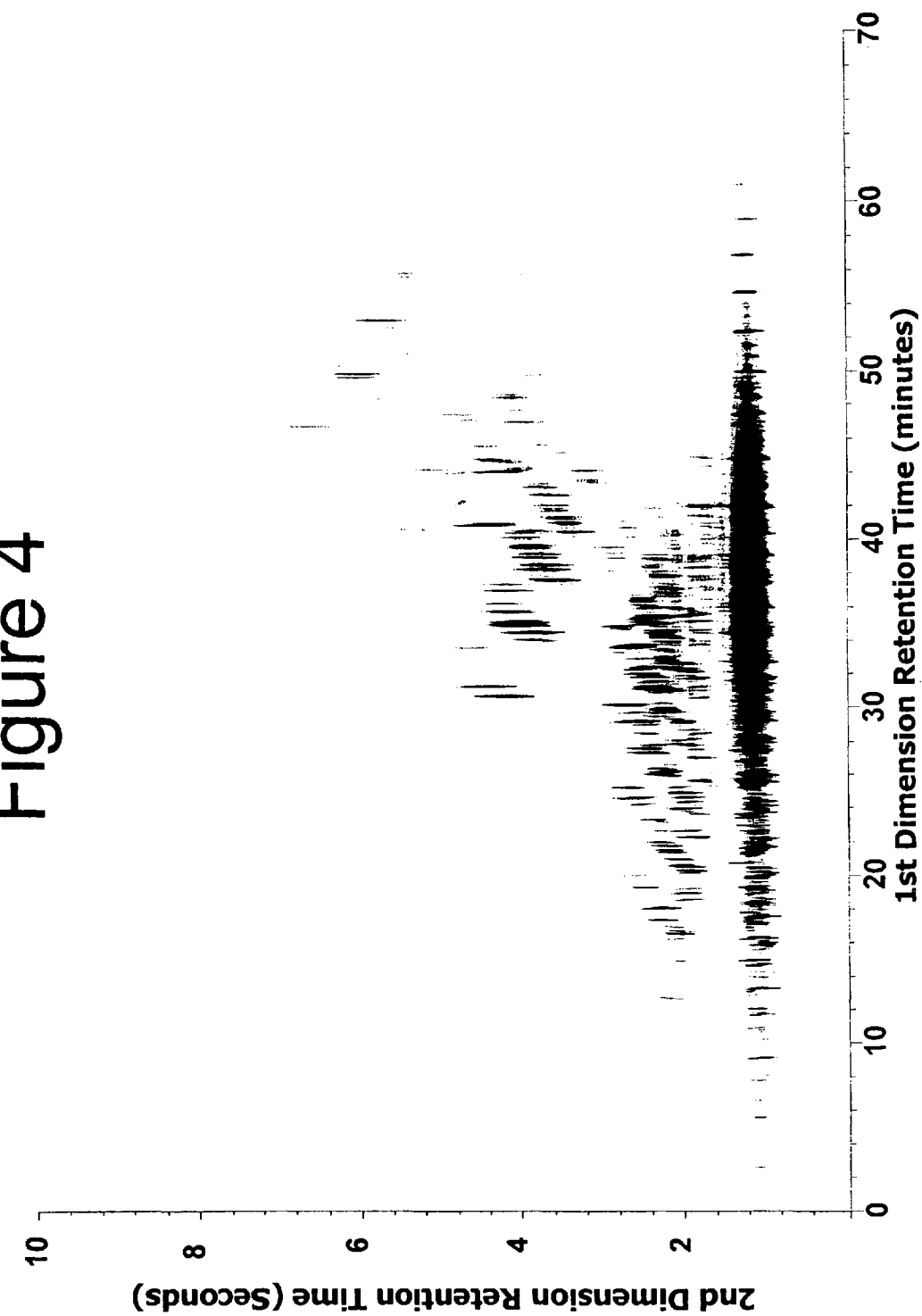
FIG. 4 shows a comprehensive two-dimensional gas chromatogram of diesel using the valve modulation system of the present invention.

A 0.2 μL sample was injected with 50:1 split at 300° C. in constant column flow mode at 1.5 mL per minute. The oven is programmed from 36° C. with 2 minute hold and 3° C. per minute increment to 300° C. with 0 minute hold and with total run time 90 minutes. The secondary carrier gas is in constant flow at 100 mL per minute. The modulation period is 8 seconds. The sampling rate for the detector was 100 Hz. FIG. 4 is the GC×GC chromatogram of the diesel stream.

B. One Twelve-Port Two-Position Switching Valve

Figure 5:
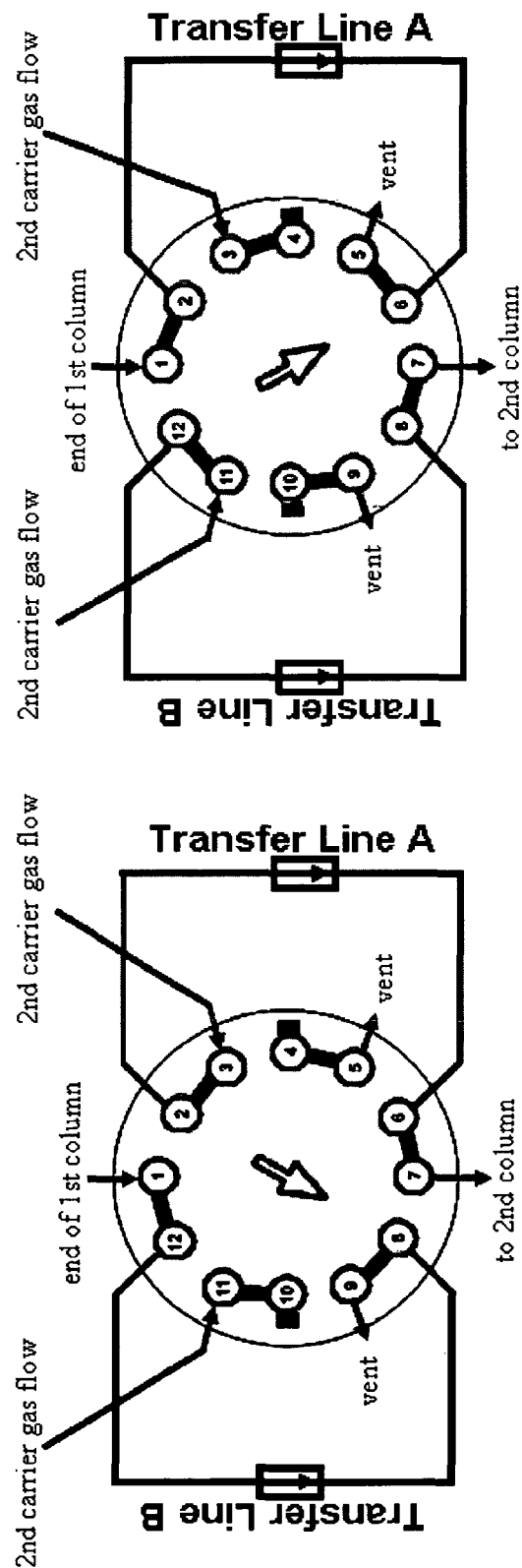
FIG. 5 shows a schematic diagram of another embodiment of the valve modulation system of the present invention.

The modulation system can also be built with one valve with at least twelve ports. FIG. 5 shows a schematic diagram of valve modulation system including only one valve. The detailed modulation process is explained below:

(1) When the valve is in the position X in one modulation period (as on the left side in FIG. 5)
(a) The eluent comes out of the first dimensional column and flows through port 1 and then passes through port 12 and deposits in transfer line B and through port 8 and port 9 to vent
(b) The secondary carrier gas flow enters port 3, passes to port 2 and sweeps the eluent deposited in transfer line A during the last modulation period through port 6 to port 7 and to the second dimensional column
(2) In the next modulation period, the valves switches to position Y (as on the right side in FIG. 5)
(a) The eluent comes out from the first dimensional column and flows through port 1 then passes through port 2 and deposits in transfer line A and through port 6 and port 5 to vent
(b) The secondary carrier gas flow passes through port 11 to port 12 and sweeps the eluent deposited in transfer line B from the last modulation period through port 8 to port 7 and to the second dimensional column.

The modulation system can also be built on one valve with more than twelve ports but because of the extra loops and ports involved, it will not perform as simple and as well as one twelve port valve.

What is claimed is:

1. A two-dimensional comprehensive Gas Chromatography system (GC×GC) having:
    (i) two columns;
    (ii) two transfer lines interchangeably connectable between the columns and
    (iii) a modulator comprising one two-position switching valve having ports switchable between two positions in each of which a carrier gas flow is maintained through both columns.

2. The GC×GC of claim 1 wherein the modulator comprises one eight-port two-position switching valve as the modulator.

3. The GC×GC of claim 1 wherein the modulator comprises one twelve-port two-position switching valve as the modulator.

4. The GC×GC of claim 1 which includes means for controlling the flow rate through the second dimensional column independently.

5. The GC×GC of claim 1 which includes means for controlling the temperature of the second dimensional column temperature independently.

6. The GC×GC of claim 1 which includes a source of carrier gas.

7. The GC×GC of claim 6 in which the two-position switching valve is switchable between:
    a first position in which carrier gas passes (a) from the carrier gas source through the first of the two columns and from the end of the first column through a first transfer line to vent and (b) from the carrier gas source through the second of the two transfer lines to the entry of the second of the two columns and
    a second position in which carrier gas passes (c) from the carrier gas source through the first of the two columns and from the end of the first column through the second transfer line to vent and (d) from the carrier gas source through the first transfer line to the entry of the second column.

* * * * *